United States Patent [19]

Schrader et al.

[11] Patent Number: 4,941,742
[45] Date of Patent: Jul. 17, 1990

[54] ARRANGEMENT FOR MEASURING THE CONCENTRATION OF GASEOUS AND VAPOROUS COMPONENTS OF A FLUID MIXTURE

[75] Inventors: Bernhard Schrader; Petra Heinrich, both of Essen; Raimund Wyzgol, Dortmund, all of Fed. Rep. of Germany

[73] Assignee: Drägerwerk Aktiengesellschaft, Lübeck, Fed. Rep. of Germany

[21] Appl. No.: 288,309

[22] Filed: Dec. 22, 1988

[30] Foreign Application Priority Data

Dec. 23, 1987 [DE] Fed. Rep. of Germany ....... 3743684

[51] Int. Cl.⁵ .................. G01N 1/10; G01N 21/05
[52] U.S. Cl. ........................... 356/38; 250/576; 356/440
[58] Field of Search ............ 356/36, 38, 440; 250/304, 573, 576

[56] References Cited

U.S. PATENT DOCUMENTS 3,654,801  4/1972  Keefer et al. ............... 356/38 X
4,135,100  1/1979  Harada et al. ............... 356/440 X

FOREIGN PATENT DOCUMENTS 3344019  6/1985  Fed. Rep. of Germany .
53-29192  3/1978  Japan ........................ 356/440
409267  7/1932  United Kingdom ............ 250/576

Primary Examiner—Vincent P. McGraw
Attorney, Agent, or Firm—Walter Ottesen

[57] ABSTRACT

The invention relates to an arrangement for measuring the concentration of gaseous and/or vaporous components of a fluid mixture by means of light absorption such as by means of an infrared absorption by utilizing a membrane which is made of a material in which the component of the fluid mixture to be measured accumulates. The membrane is transparent to the measuring radiation and is selectively permeable for the particles of the compounds to be measured. The membrane further acts on the radiation path between the light source and the detector. The arrangement is improved with respect to selectivity and the detection sensitivity. This is achieved in that the membrane is mounted in the flow path of the fluid mixture such that the flow path is subdivided into two component paths at the surfaces of the membrane.

7 Claims, 5 Drawing Sheets

ARRANGEMENT FOR MEASURING THE CONCENTRATION OF GASEOUS AND VAPOROUS COMPONENTS OF A FLUID MIXTURE

FIELD OF THE INVENTION

The invention relates to an arrangement for measuring the concentration of gaseous and/or vaporous components of a fluid mixture by light absorption such as by means of infrared absorption with the use of a membrane which is made of a material in which the component of the fluid mixture to be measured accumulates. The membrane is selectively permeable for particles of the component to be measured and is transparent to the measuring radiation. This membrane is effective in the radiation path between the light source and the detector.

BACKGROUND OF THE INVENTION

It is necessary to measure the concentration of gaseous and vaporous components of a fluid mixture comprising gases or gases and vapors or exclusively vapors for the various technical applications such s for monitoring workplaces which can include locations where washing is done with solvents such as in a chemical cleaning facility and operating rooms. However, this measurement can also be used for process control such as in chemical facilities and in the case of measuring breathing gas. The fluid mixture to be measured can comprise gases or gases and vapors or can be comprised exclusively of vapors. If required, the fluid mixture can also be monitored.

An arrangement for optically measuring material concentrations in fluid mixtures is disclosed in German published patent application DE-OS 3,344,019. In the arrangement disclosed in this publication, a measuring chamber made of a material which is transparent to the measuring radiation is provided for the optical measurement of material concentrations in the infrared range. The material is selectively permeable for the particles to be measured and interacts with the particles. This material defines a functional connection with the measuring object and the measurement radiation radiates therethrough. At the same time, it is provided that the particles to be measured accumulate in the membrane. The advantage of this arrangement is seen in that the selectivity and sensitivity of the measurement is increased by means of the accumulation of the particles to be measured in the membrane while being separated from other particles which are not to be measured and which can, however, be disturbing.

Summary of the Invention

It is an object of the invention to provide an arrangement for measuring the concentration of gaseous and/or vaporous components of a fluid mixture with an increased sensitivity of the components to be measured. It is a salient feature of the invention that the membrane is arranged in the flow path of the fluid mixture such that the flow path is divided into two component paths on the surfaces of the membrane. With such an arrangement, the reaction of the particles to be detected during the same reaction time is increased and the detectability is improved. With such an increased accumulation of the gaseous or vaporous components of the fluid mixture, their many weak components of the bands occurring in a broad range are melted together to a narrow intense band for the same integral extinction coefficient. In this way, the danger of an overlapping with disturbing bands of other fluid components is reduced. As a consequence of the increased accumulation and of the band contraction, the required optical path length with respect to previously known infrared paths is substantially reduced. Disturbing absorption bands occur with less effect, for example, the bands of $H_2O$ in the ranges of absorption of carbonyl groups.

Since the accumulation by the membrane occurs selectively, the transverse sensitivity becomes simultaneously less with respect to the components which are not intended to be accumulated.

Pursuant to a preferred embodiment of the invention, the membrane is mounted so as to be movable relative to the light source and to the detector. The membrane can be made from various materials in accordance with the substances which are to be accumulated. The membrane can also be made in various configurations. A circular disc-shaped configuration appears to be a preferred embodiment as well as the utilization of the membrane as a continuous tape or as a tape for which a flow can be on both sides thereof.

It is advantageous to provide non-transparent sections in the membrane for comparative measurements with the purpose of eliminating drifts in the light source and the detector such as by means of a quotient formation of the measuring signal. In this way, the zero indication can be determined for each instance and can be corrected by known electronic control circuits as may be required. The membrane can also advantageously have sections of different thicknesses.

By using a membrane movable relative to the light source and the detector, the advantage is afforded that no reference beam or reference cuvette is necessary for calibration purposes or to eliminate sensor o detector drift as is necessary with known double ray spectrometers. When rotating a membrane disc or for the transport of a membrane tape, it is simply necessary to alternate between membrane sections of different thicknesses. In this way, all disturbing measuring effects can be eliminated which are not connected with taking up particles in the membrane to be detected. Such disturbing measurement effects include the following: the drift of sensors and detectors, further surface characteristics of the membrane and contamination of the surface.

Pursuant to another embodiment of the invention wherein the selectivity is increased, the membrane can include sections wherein different components accumulate.

For this embodiment, the membrane can be configured to have sector discs or aperture discs. If required, the membrane material can be mounted in a metal frame when no adequate support for the freely suspended disc configuration is present. The movement of the membrane disc can be rotative in one direction or can be a pendular movement in a predetermined angular range. It is also possible to mount the membrane in a circularly-shaped frame without a central shaft and that this frame is so configured that it is movable by means of support and drive rollers which engage the frame at the periphery thereof.

An advantageous embodiment can be configured so that the light source is mounted on one side of a flow space in which the membrane is accommodated and that the detector is provided on the other side of the flow space. In this configuration, the membrane is mounted so that it is parallel to the main flow direction within the flow space and is mounted so as to be essentially perpendicular to the beam path between light source and detector.

It is advantageous to configure this embodiment so that the rays of the light beam in the flow space are essentially parallel.

In a further embodiment of the invention, the light source can be mounted at the focal point of a first mirror (parabolic, spherical or elliptical) whose beam path is directed toward the flow space from one side and that on the other side of the flow space, a second similar mirror is mounted and aligned in correspondence to the first mirror. This second mirror accommodates the detector at its focal point. The flow space then consists of flow paths arranged on respective sides of the membrane and t which the membrane is symmetrically mounted.

An advantageous further embodiment can, however, also be provided in that the light source is mounted ahead of a first lens which converts the radiation emanating from the light source into a parallel bundle of rays passing through the flow space and that a second lens is mounted on the side of the detector by means of which the parallel bundle of rays exiting from the flow space is concentrated in a focal point and taken up by the detector. In lieu of single lenses, respective lens systems having an appropriate effect can also be utilized.

The light source and detector can advantageously be accommodated in a closed protective gas chamber formed from mirror parts with the chamber on the side of the light source being closed off with an optical filter and the chamber on the detector side being closed off with an infrared permeable window.

A further advantageous configuration is provided by mounting a reflecting surface in the region of the membrane and that the light source and detector both lie on the same side of the membrane.

An additional advantage can be achieved in that an arrangement can be provided for introducing a reference gas into the flow space.

As an example of an advantageous membrane material, the membrane can be made of silicone rubber for measuring concentrations of carbon disulphide. More specifically, the carbon disulphide becomes reversibly dissolved in the membrane made of silicone rubber without the chemical characteristics of the carbon disulphide or silicone becoming changed.

The advantage here is that the silicone membrane selectively accumulates carbon disulphide while water from the ambient does not become dissolved in the silicone. In this way, an optical measurement signal such as a vibrational spectrum of carbon disulphide can be clearly distinguished from an undesired water spectrum. For an optical measurement in air, the water spectrum would obscure the spectrum of carbon disulphide at low concentrations and make it unrecognizable. Accordingly, and in this way, the invention makes a measurement process possible which is more sensitive.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
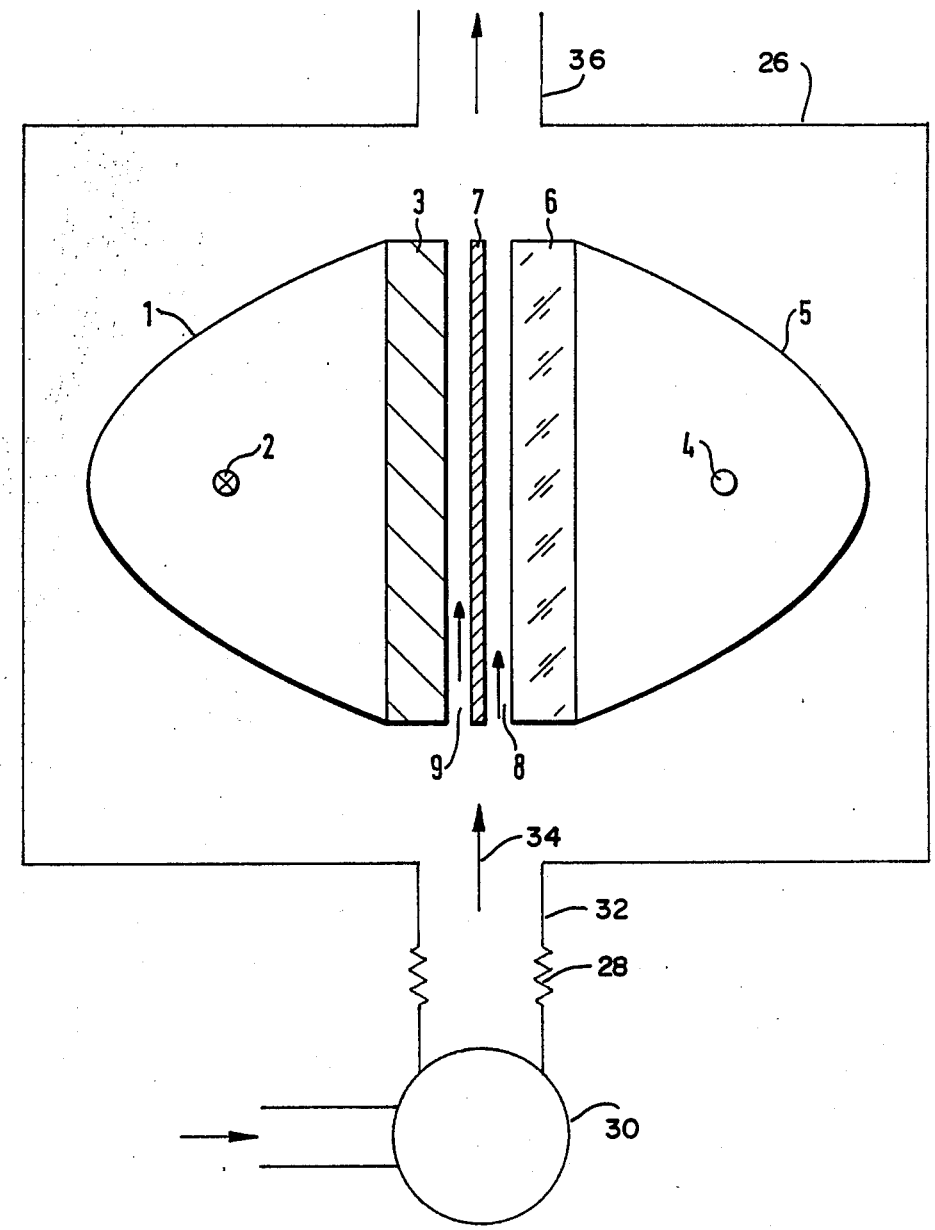
FIG. 1 is a transverse section taken through a measuring arrangement having a stationary membrane.

In the embodiment of FIG. 1, a light source 2 is mounted in a first parabolic mirror 1 with the light source being preferably configured as an infrared radiator. The space defined by the first parabolic mirror 1 is delimited by an optical filter 3 so that a closed chamber is provided which can be filled with protective gas as may be required. On the receiving side, an infrared detector 4 is located at the focal point of a second parabolic mirror 5. The parabolic mirror 5 and a window 6 permeable to infrared radiation conjointly define a closed chamber and this chamber can be filled, as may be required, with a protective gas such as nitrogen. The detector 4 can be a photoresistor or pyroelectric sensor or a thermoelement can, for example, be used.

The parabolic mirrors 1 and 5 and the membrane 7 are arranged in a housing 26 which is opaque to protect the arrangement against stray light which could otherwise interfere with the optical measurements.

The gas to be measured is pumped into the housing 26 through a hose 28 by a pump 30. The hose 28 is connected to an inlet duct 32 of the housing and a flow of the gas to be measured is directed to the two flow gaps (8, 9) as indicated by arrow 34.

The flow path in which a membrane 7 is disposed is formed by two flow gaps (8, 9) on respective sides thereof with the membrane being configured to accumulate the component to be measured. The thickness of these flow gaps as well as the membrane thickness is generally less than 1 mm. The flow of the fluid mixture is indicated by respective arrows shown in displaced relationship to each other. After passing through the flow gaps (8, 9), the gas is vented to the ambient via an outlet duct 36.

In the embodiment shown in FIG. 1, the membrane 7 can be configured as a removable insert part mountable in an appropriate holder. During operation of the measuring arrangement, the light source 2 emits an appropriate light radiation containing the desired infrared component which is redirected by means of the first parabolic mirror 1 into what is essentially a parallel radiation passing through the optical filter 3. This infrared radiation passes through the flow space formed by the two gap spaces (8, 9) and through the membrane 7 and reaches the inner surface of the second parabolic mirror 5 via the infrared-permeable window 6. The light radiation is then concentrated and arrives at the detector 4 mounted at the focal point. The circuit configuration of the measuring apparatus corresponds to known configurations.

Figure 2:
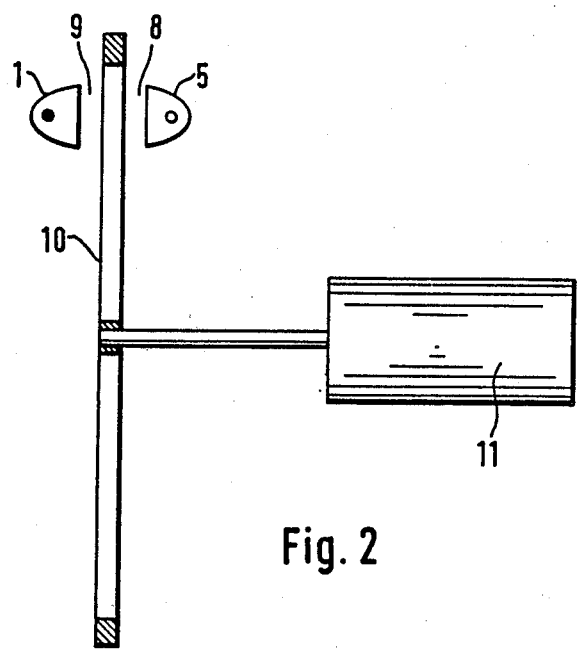
FIG. 2 is an alternate embodiment wherein the membrane is in the form of a circular membrane disc driven about its longitudinal axis by means of an electric drive motor.

In FIG. 2, a circularly-shaped membrane disc 10 is shown which can be driven by an electrical drive motor 11. The light radiation between the first mirror 1 on the transmitting side and the second mirror 5 on the receiving side penetrates an annular region of the membrane disc 10.

Figure 3:
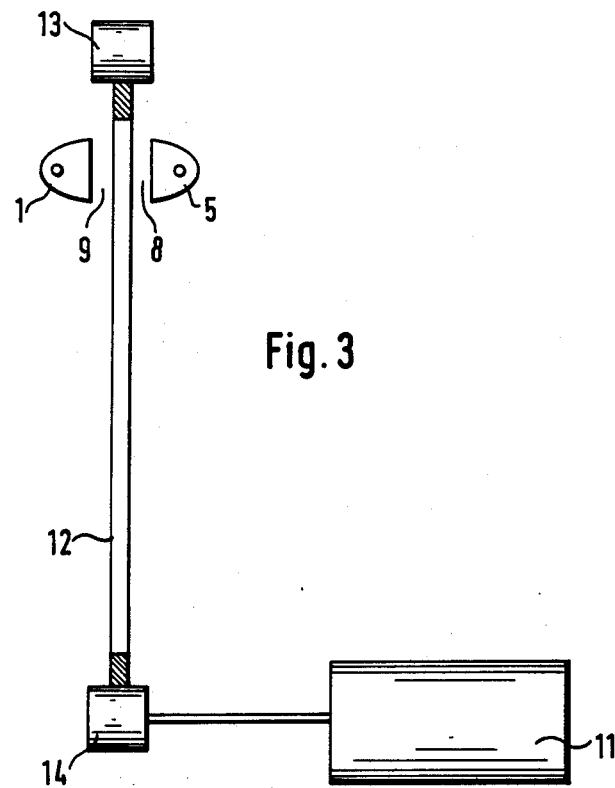
FIG. 3 is a membrane corresponding to that of FIG. 2 except that here the circularly-shaped membrane disc is driven at the peripheral edge thereof.

The embodiment of FIG. 3 corresponds to that shown in FIG. 2 with respect to the optical configuration; however, the membrane disc 12 is supported by rollers 13 distributed about the periphery thereof and is driven by one such peripheral roller 14. In this way, the use of a center shaft is avoided.

Figure 4:
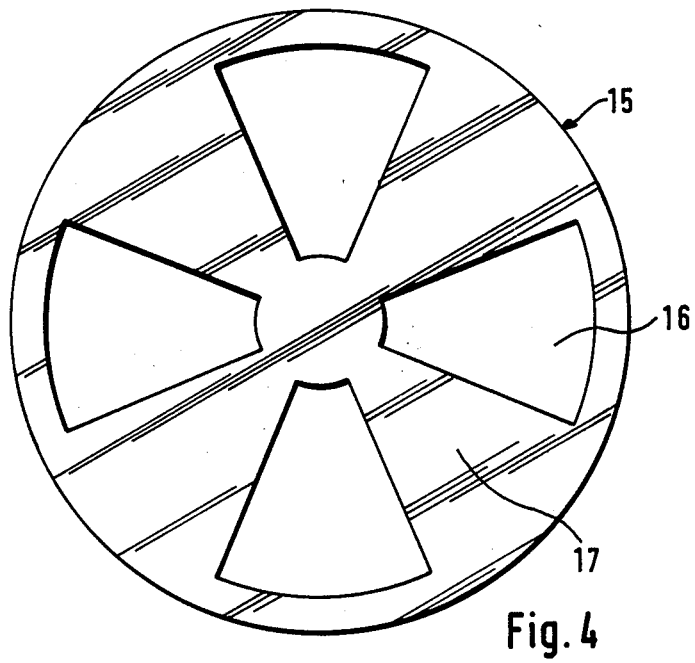
FIG. 4 is a plan view of a membrane disc for use in a measuring arrangement according to FIGS. 2 or 3 with the membrane disc being provided with sector regions.

The plan view of FIG. 4 shows a membrane disc 15 which includes sector sections 16 made of membrane material and intermediate sections 17 which are optically non-transparent. In accordance with the selected rotational speed of the membrane disc 15, measurement signals and correcting signals can be generated for compensating for drift occurrences in a repetition rate favorable for further processing.

Figure 5:
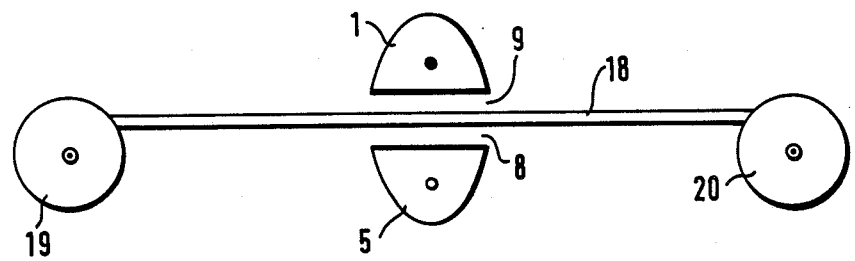
FIG. 5 shows a measuring arrangement corresponding to that of FIG. 1 with the membrane configured as a tape over which the fluid mixture flows on both sides thereof.

FIG. 5 is another embodiment of the invention wherein the membrane 18 is configured as a tape. The tape-shaped membrane 18 can either be unrolled at a non-reversible storage unit or it can be arranged in a reversible configuration between two reels (19, 20).

Figure 6:
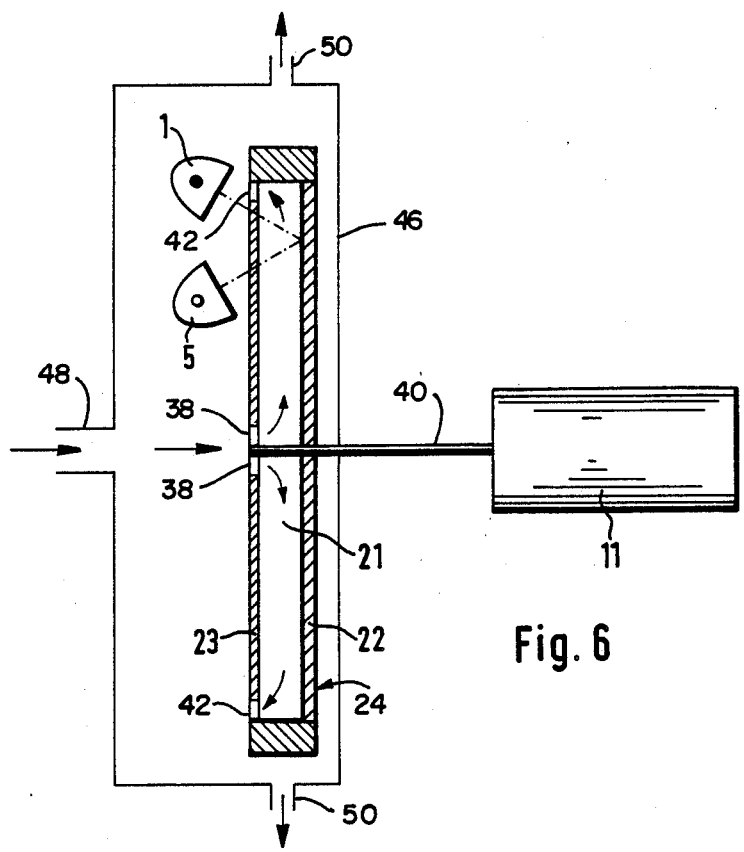
FIG. 6 is an alternate embodiment wherein the membrane is mounted in front of a reflecting carrier disc; and, FIG. 7 shows a measuring arrangement wherein the membrane is configured as a movable tape and wherein the tape is subjected to the fluid mixture at a location remote from the location at which the optical measurements are made.

FIG. 6 shows an embodiment which includes a carrier disc 24 defining a hollow space 21 and having a reflecting layer 22. A circularly-shaped membrane 23 is disposed over this reflecting surface 22 and contains a plurality of inlet openings 38 disposed in the immediate vicinity of the drive shaft 40 of drive motor 11. The membrane 23 further has a plurality of outlet openings 42 at its outer periphery. The gas to be measured is drawn into the hollow space 21 by suction along the axis of drive shaft 40 as indicated by arrow 44 and is expelled through outlet openings 42. The carrier disc 24 can be mounted for rotation inside the housing 46 and the gas to be measured is drawn into the latter through inlet duct 48 and vented to the ambient through outlet ducts 50. The first and second mirrors (1, 5) are mounted on the same side of the membrane 23 and within the housing 46.

If required, only mirror half portions can be used on the connecting line between the light source 2 and the detector 4 in lieu of the rotationally symmetrical parabolic mirrors shown above. In the embodiment of FIG. 4, the sector segments 16 can be configured to have different thicknesses and/or be configured for different components to be accumulated.

In the above examples, the light source and detector were so arranged that the beam path and the optical measuring location lie in the flow path of the fluid mixture. However, it can be advantageous to provide the optical measuring location outside of the region where the fluid mixture is applied to the membrane. This affords the possibility to first charge the membrane outside of the beam path with the fluid mixture, for example, by dipping the membrane in a liquid fluid mixture or by blowing a gaseous fluid mixture directly on the membrane. Thereafter, excess quantities of the charge can be stripped off of the membrane and the actual measurement can then be conducted at a remote location under controlled conditions.

Figure 7:
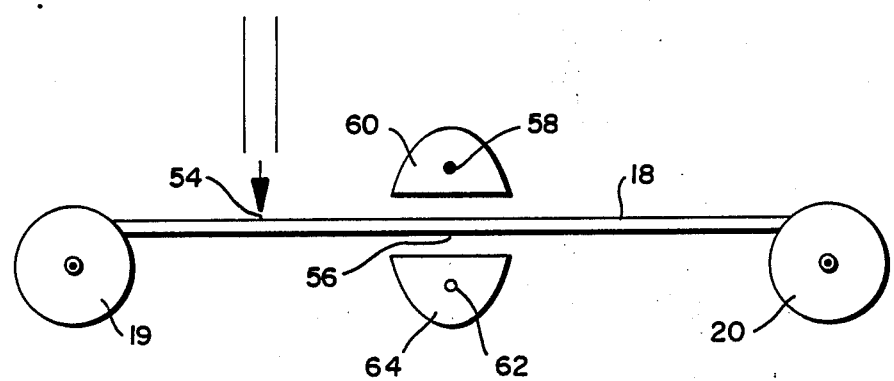

In FIG. 7, a membrane in the form of a moving tape is subjected to the fluid mixture at the location identified by reference numeral 54 and is measured at location 56 by means of the light source 58 mounted in parabolic mirror 60 and detector 62 mounted in parabolic mirror 64.

It is understood that the foregoing description is that of the preferred embodiments of the invention and that various changes and modifications may be made thereto without departing from the spirit and scope of the invention as defined in the appended claims.

What is claimed is:

1. An arrangement for measuring the concentration of gaseous and/or vaporous components of a flowing fluid mixture, the arrangement comprising:
   light source means for irradiating light radiation and directing the same along a predetermined light radiation path;
   detecting means mounted downstream of said light source means for receiving said light radiation;
   flow path means for conducting said flow of said fluid mixture through said light radiation path;
   a membrane having two surfaces and being disposed in said flow path means so as to subdivide the latter into two component flow paths for conducting respective component flows of said fluid mixture over respective ones of said surfaces;
   said membrane being transparent to said light radiation and being selectively permeable to particles of said components to be measured for accumulating the latter and so act upon said light radiation moving along said light radiation path;
   said light source means and said detecting means being mounted adjacent corresponding ones of said surfaces of said membrane so as to conjointly define said component flow paths with said membrane and so as to cause said light radiation path to be substantially perpendicular to said membrane; and,
   said membrane being mounted in said flow path means so as to be parallel to the flow of said fluid mixture.

2. The arrangement of claim 1, said light source means including directing means for directing said light radiation along said light radiation path as a plurality of substantially mutually parallel light rays in the region of said flow path means.

3. The arrangement of claim 1, said light source means including: a first mirror mounted on one side of said flow path means and defining a first focal point; and, a light source mounted at said first focal point; said first mirror being configured so as to direct said light radiation toward said component flow paths as a plurality of substantially mutually parallel light rays; and, said detecting means including: a second mirror mounted on the other side of said flow path means and configured to correspond to said first mirror, said second mirror defining a second focal point; and, a detector mounted at said second focal point.

4. The arrangement of claim 1, said light source means disposed on one side of said flow path means and including: a first lens; and, a light source mounted ahead of said first lens; said first lens being configured so as to transform the radiation emitted by said light source into a bundle of parallel rays passing through said component flow paths; and, said detecting means disposed on the other side of said flow path means and including: a second lens defining a focal point and being configured so as to concentrate said bundle of parallel rays onto said focal point; and, a detector mounted a said focal point for receiving the concentrated rays.

5. The arrangement of claim 1, said light source means including: a first protective gas chamber; and, a light source mounted in said first protective gas chamber; and, said detecting means including: a second protective gas chamber; and, a detector mounted in said second protective gas chamber.

6. The arrangement of claim 1, comprising means for introducing a reference gas into said flow path means.

7. The arrangement of claim 1, wherein said fluid mixture contains carbon disulphide and said membrane is made of silicone rubber for measuring said carbon disulphide.

* * * * *

UNITED STATES PATENT AND TRADEMARK OFFICE
CERTIFICATE OF CORRECTION

PATENT NO. : 4,941,742

DATED : July 17, 1990

INVENTOR(S) : Bernhard Schrader, Petra Heinrich and Raimund Wyzgol

It is certified that error appears in the above-identified patent and that said Letters Patent is hereby corrected as shown below:

In the Abstract, line 9: delete "compounds" and substitute -- components -- therefor.

In column 1, line 24: delete "s" and substitute -- as -- therefor.

In column 2, line 37: delete "o" and substitute -- or -- therefor.

In column 3, line 17: delete "t" and substitute -- to -- therefor.

In column 7, line 2: delete "a", second occurrence, and substitute -- at -- therefor.

Signed and Sealed this

First Day of October, 1991

*Attest:*

HARRY F. MANBECK, JR.

*Attesting Officer*       *Commissioner of Patents and Trademarks*